United States Patent
Yi et al.

(10) Patent No.: US 11,293,050 B2
(45) Date of Patent: Apr. 5, 2022

(54) METHOD FOR MARKING 5-FORMYL CYTOSINE AND USE THEREOF IN SINGLE BASE RESOLUTION SEQUENCING

(71) Applicant: PEKING UNIVERSITY, Beijing (CN)

(72) Inventors: Chengqi Yi, Beijing (CN); Chenxu Zhu, Beijing (CN); Bo Xia, Beijing (CN)

(73) Assignee: Peking University, Beijing (CN)

(*) Notice: Subject to any disclaimer, the term of this patent is extended or adjusted under 35 U.S.C. 154(b) by 223 days.

(21) Appl. No.: 16/489,653

(22) PCT Filed: Feb. 26, 2018

(86) PCT No.: PCT/CN2018/077261
§ 371 (c)(1),
(2) Date: Aug. 28, 2019

(87) PCT Pub. No.: WO2018/157775
PCT Pub. Date: Sep. 7, 2018

(65) Prior Publication Data
US 2020/0165661 A1     May 28, 2020

(30) Foreign Application Priority Data
Feb. 28, 2017  (CN) .......................... 201710111600.9

(51) Int. Cl.
C12Q 1/68     (2018.01)
C12Q 1/6806     (2018.01)
C12Q 1/6869     (2018.01)

(52) U.S. Cl.
CPC ......... C12Q 1/6806 (2013.01); C12Q 1/6869 (2013.01)

(58) Field of Classification Search
CPC ............................ C12Q 1/6806; C12Q 1/6869
See application file for complete search history.

(56) References Cited

U.S. PATENT DOCUMENTS

| | | | | |
|---|---|---|---|---|
| 10,519,184 B2 * | 12/2019 | Yi | ........................ | C12Q 1/6858 |
| 2016/0362438 A1 * | 12/2016 | Yi | ........................ | C12Q 1/6869 |

FOREIGN PATENT DOCUMENTS

| | | |
|---|---|---|
| CN | 103060450 B | 4/2013 |
| CN | 103305621 A | 9/2013 |
| CN | 104311618 A | 1/2015 |
| CN | 106957350 A | 7/2017 |
| JP | H09263584 A | 10/1997 |
| WO | 8701373 A1 | 3/1987 |
| WO | 2015043493 A1 | 4/2015 |

OTHER PUBLICATIONS

Chen, Jinlong, "The Principle and Process of Fine Organic Synthesis," China Light Industry Press, Apr. 1992, p. 260.

* cited by examiner

Primary Examiner — Jezia Riley
(74) Attorney, Agent, or Firm — Umberg Zipser LLP; Jason Tejani

(57) ABSTRACT

Disclosed are a method for marking 5-formyl cytosine and the use thereof in single base resolution sequencing. The method for marking the 5-formyl cytosine comprises the following steps of: (1) preparing a DNA or RNA sample; and (2) mixing the DNA or RNA sample with a buffer solution and a compound $R_1$—$CH_2$—CN to obtain a marking reaction system; and reacting the compound $R_1$—$CH_2$—CN therein with the 5-formyl cytosine in DNA and RNA molecules, and thereby achieving the marking of the 5-formyl cytosine; the reaction process is as in (I) below:

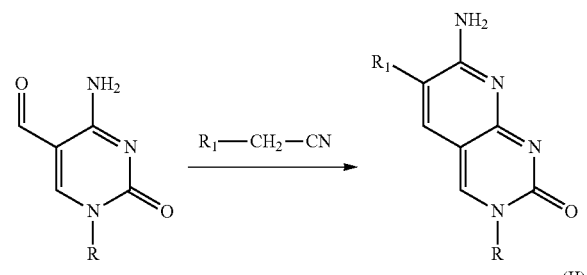

wherein, $R_1$ is an electron withdrawing group next to the $CH_2$ group, preferably —CN, (II) or (III), and more preferably —CN; R is a DNA or RNA molecule connected to the 5-formyl cytosine; and the pH value of the marking reaction system is 7.5-9. On this basis, also provided in the present invention is a sequencing analysis method for the 5-formyl cytosine. The method can be implemented at a single cell level, and can achieve the sequencing of single-base resolution levels.

19 Claims, 4 Drawing Sheets

Specification includes a Sequence Listing.

SEQUENCE LISTING

<160> NUMBER OF SEQ ID NOS: 11

<210> SEQ ID NO 1
<211> LENGTH: 76
<212> TYPE: DNA
<213> ORGANISM: Artificial Sequence
<220> FEATURE:
<223> OTHER INFORMATION: 5fC-76mer
<220> FEATURE:
<221> NAME/KEY: 5-formyl cytosine
<222> LOCATION: (38)..(38)

<400> SEQUENCE: 1
cctcaccatc tcaaccaata ttatattacg cgtatatcgc gtatttcgcg ttataatatt      60
gagggagaag tggtga      76

<210> SEQ ID NO 2
<211> LENGTH: 27
<212> TYPE: DNA
<213> ORGANISM: Artificial Sequence
<220> FEATURE:
<223> OTHER INFORMATION: forward primer

<400> SEQUENCE: 2
cctcaccatc tcaaccaata ttatatt                                    27

<210> SEQ ID NO 3
<211> LENGTH: 80
<212> TYPE: DNA
<213> ORGANISM: Artificial Sequence
<220> FEATURE:
<223> OTHER INFORMATION: reverse primer

<400> SEQUENCE: 3
ctccgacatt atcactacca tcaaccaccc atcctacctg gactacattc ttattcagta    60
ttcaccactt ctccctcaat                                              80

<210> SEQ ID NO 4
<211> LENGTH: 20
<212> TYPE: DNA
<213> ORGANISM: Artificial Sequence
<220> FEATURE:
<223> OTHER INFORMATION: sequencing primer

<400> SEQUENCE: 4
ctccgacatt atcactacca                                              20

<210> SEQ ID NO 5
<211> LENGTH: 35
<212> TYPE: DNA
<213> ORGANISM: Artificial Sequence
<220> FEATURE:
<223> OTHER INFORMATION: MALBAC Primer
<220> FEATURE:
<221> NAME/KEY: misc_feature
<222> LOCATION: (28)..(35)
<223> OTHER INFORMATION: n is a, c, g, or t

<400> SEQUENCE: 5
gtgagtgatg gttgaggtag tgtggagnnn nnnnn                             35

<210> SEQ ID NO 6
<211> LENGTH: 58
<212> TYPE: DNA
<213> ORGANISM: Artificial Sequence
<220> FEATURE:
<223> OTHER INFORMATION: linker sequence

<400> SEQUENCE: 6
aatgatacgg cgaccaccga gatctacact ctttccctac acgacgctct tccgatct     58

<210> SEQ ID NO 7
<211> LENGTH: 63
<212> TYPE: DNA
<213> ORGANISM: Artificial Sequence
<220> FEATURE:
<223> OTHER INFORMATION: complementary chain of linker sequence

<400> SEQUENCE: 7
gatcggaaga gcacacgtct gaactccagt cacatcacga tctcgtatgc cgtcttctgc    60
ttg                                                                63

<210> SEQ ID NO 8
<211> LENGTH: 20
<212> TYPE: DNA
<213> ORGANISM: Artificial Sequence
<220> FEATURE:
<223> OTHER INFORMATION: forward primer

<400> SEQUENCE: 8
aatgatacgg cgaccaccga                                           20

<210> SEQ ID NO 9
<211> LENGTH: 21
<212> TYPE: DNA
<213> ORGANISM: Artificial Sequence
<220> FEATURE:
<223> OTHER INFORMATION: reverse primer

<400> SEQUENCE: 9
caagcagaag acggcatacg a                                         21

<210> SEQ ID NO 10
<211> LENGTH: 137
<212> TYPE: DNA
<213> ORGANISM: Artificial Sequence
<220> FEATURE:
<223> OTHER INFORMATION: pattern sequence with 5fC
<220> FEATURE:
<221> NAME/KEY: 5-formyl cytosine
<222> LOCATION: (38)..(38)

<400> SEQUENCE: 10
cctcaccatc tcaaccaata ttatattacg cgtatatcgc gtatttcgcg ttataatatt    60
gagggagaag tggtgaatac tgaataagaa tgtagtccag gtaggatggg tggttgatgg   120
tagtgataat gtcggag                                                 137

<210> SEQ ID NO 11
<211> LENGTH: 137
<212> TYPE: DNA
<213> ORGANISM: Artificial Sequence
<220> FEATURE:
<223> OTHER INFORMATION: pattern sequence without 5fC

<400> SEQUENCE: 11
cctcaccatc tcaaccaata ttatattacg cgtatatcgc gtatttcgcg ttataatatt    60
gagggagaag tggtgaatac tgaataagaa tgtagtccag gtaggatggg tggttgatgg   120
tagtgataat gtcggag                                                 137

METHOD FOR MARKING 5-FORMYL CYTOSINE AND USE THEREOF IN SINGLE BASE RESOLUTION SEQUENCING

CROSS-REFERENCE TO RELATED APPLICATION(S)

The present application claims priority to International Application No. PCT/CN2018/077261 filed on Feb. 26, 2018 which claims the priority of Chinese Patent Application No. 201710111600.9, filed before the CNIPA on Feb. 28, 2017, entitled "METHOD FOR LABELING 5-FORMYL CYTOSINE AND USE THEREOF IN SINGLE BASE RESOLUTION SEQUENCING", which is herein incorporated by reference in its entirety.

INCORPORATION BY REFERENCE

The present application contains a Sequence Listing which has been submitted in ASCII format via EFS-Web and is hereby incorporated by reference in its entirety. Said ASCII copy was amended on Nov. 12, 2019, is named 104140_0003USSEQLISTING.txt, and is 3,076 bytes in size.

FIELD OF THE INVENTION

The invention relates to the technical filed of labeling 5-formyl cytosine, in particular to a method for labeling 5-formyl cytosine and the use thereof in single-base resolution sequencing.

BACKGROUND OF THE INVENTION

DNA methylation and demethylation studies are among the most important research subjects in the field of epigenetics. The methylation and demethylation regulation of the gene regulatory region relates to the activation and inhibition of expression of downstream genes, thereby involved in the corresponding biological processes. In mammals, methylation of DNA mainly occurs at the $5^{th}$ position of cytosine to form 5-methylcytosine (5mC). The demethylation of 5mC is accomplished by oxidation of the TET (Ten-Eleven Translocation) family of proteins. 5mC can be iteratively oxidized to produce 5-hydroxymethylcytosine (5hmC), 5-formylcytosine (5fC) and 5-carboxylcytosine (5caC), and 5fC and 5caC can then be excised by endonucleases via the base excision repair pathway to generate a unmodified cytosine, known as active demethylation of DNA (Mamta Tahiliani, et al., *Science*, 2009, 324:931-935; Skirmantas Kriaucionis and Nathaniel Heintz, *Science*, 2009, 324:929-930; Toni Pfaffeneder, et al., *Angewandte Chemie International Edition*, 2011, 123:7146-7150; Shinsuke Ito, et al., *Science*, 2011, 333:1300-1303; Yufei He, et al., *Science*, 2011, 333:1303-1307).

In order to study the biological function of this kind of epigenetically modified bases, it is important to understand their genomic distribution as well as the specific sequence contents. A golden-standard method for DNA methylation analysis is Bisulfite Sequencing, which can identify 5mC sequence information at single-base resolution. After treatment with sodium bisulfite, the unmodified cytosine (C) in the genome is converted to uracil (U), after amplification by polymerase chain reaction (PCR), they can then read as thymine (T) during sequencing. Due to the presence of methyl with electron-donating effect at 5 position of 5mC, it is difficult to undergo deamination for 5mC during the sodium bisulfite treatment process. Therefore, the readout for such bases is still C during PCR amplification and sequencing (Michael J. Booth, et al., *Science*, 2012, 336:934-937). In addition to DNA methylation, 5hmC, 5fC and 5caC, are modified bases that can stably present in the genome, may also have unique biological functions. Thus, it is essential to identify the distribution of these three cytosine derivatives in the genome for exploring the function thereof. However, the discovery of 5hmC, 5fC and 5caC makes Bisulfite Sequencing more complicated. For example, generally, during Bisulfite Sequencing, 5hmC is resistant to bisulfite treatment and is therefore read as C, while both 5fC and 5caC are read as T (Michael J. Booth, et al., *Science*, 2012, 336:934-937). In order to distinguish these cytosine derivatives, novel single-base resolution sequencing techniques need to be developed to identify the location of these newly modified bases in the genome. There have been some studies on 5-formyl cytosine based on chemical reactions, which focused on the formyl group at 5 position on the cytosine ring of 5fC. The researchers designed a reaction with respect to the formyl of 5fC on the basis that formyl can react with the amino of hydroxylamine compound and produce oxime (Shinsuke Ito, et al., *Science*, 2011, 333:1300-1303; Eun-Ang Raiber, et al., *Genome Biology*, 2012, 13:R69; Chunxiao Song, et al., *Cell*, 2013, 153:678-691). This reaction is used to detect the position of 5fC in genome. A method for labeling 5fC with a fluorescence group is developed using the reaction between formyl and amino (Jianlin Hu, et al., *Chemistry—A European Journal*, 2013, 19:5836-5840). The formyl group is reduced to hydroxymethyl group with $NaBH_4$, so that 5fC is reduced to 5hmC and thus is read as C during Bisulfite Sequencing process. Therefore, the position of 5fC base can also be identified in a specific region (Chunxiao Song, et al., *Cell*, 2013, 153:678-691; Michael J. Booth, et al., *Nature Chemistry*, 2014, 6:435-440). Unfortunately, none of these methods are applicable to the detection of 5fC from single cell. Therefore, there is a need to develop a novel 5fC labeling and detection method with high biocompatibility and sensitivity that is applicable to single-cell level. This is critical for further promoting the research of active DNA demethylation, and also significant for epigenetic research in the field of clinical detection as well as disease diagnosis and treatments (such as embryos, cancer cells, etc.).

Sequencing techniques for DNA epigenetic modification at the single-cell level are currently focused on 5mC and 5hmC. Single-cell 5mC sequencing technique is based on sodium bisulfite treatment (Hongshan Guo, et al., *Genome Research*, 2013; Sebastien A Smallwood, et al., *Nature Methods*, 2014; Matthias Farlik, et al., *Cell Reports*, 2015). Approximately 18% of CpG sites can be stably detected by optimizing the sodium bisulfite treatment and library construction process (Sebastien A Smallwood, et al., Nature Methods, 2014). Sequencing techniques based on sodium bisulfite treatment are not suitable for identification of 5fC in single-cell genomes, since the content of 5fC in the single-cell genome is very low compared to that of 5mC, and sodium bisulfite treatment will result in degradation of a large amount of DNA. Therefore, providing a sequencing method suitable for 5fC in a single-cell genome is an urgent problem to be solved in the art.

SUMMARY OF THE INVENTION

An object of the examples of the present invention is to provide a method for labeling 5-formyl cytosine and use thereof in single-base resolution sequencing, to detect 5-formyl cytosine in DNA or RNA at single-cell level and single-base resolution. The specific technical solutions are as follows.

The present invention provides a method for labeling 5-formyl cytosine, comprising:

(1) preparing a DNA or RNA sample;

(2) mixing the DNA or RNA sample with a buffer solution and a compound of formula $R_1$—$CH_2$—CN to obtain a labeling reaction system; and reacting the compound of formula $R_1$—$CH_2$—CN with 5-formyl cytosine in a DNA and RNA molecule to label 5-formyl cytosine; the reaction process is:

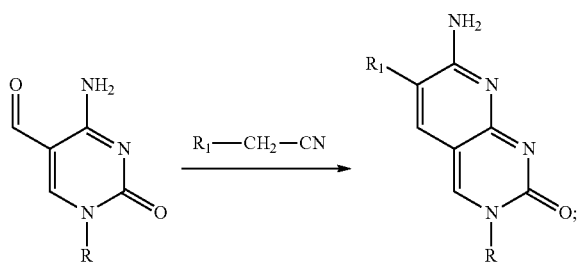

wherein, $R_1$ is an electron withdrawing group adjacent to $CH_2$, preferably —CN,

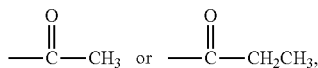

and more preferably —CN; R is a DNA or RNA molecule linked to 5-formyl cytosine; and the labeling reaction system has a pH of 7.5-9.

In a preferred embodiment, the labeling reaction system has a pH of 8-9, preferably a pH of 8.

In a preferred embodiment, the concentration of the compound of formula $R_1$—$CH_2$—CN in the labeling reaction system is in the range from 75 mM to 1500 mM, preferably from 75 mM to 1000 mM, more preferably from 75 mM to 500 mM, and most preferably 150 mM.

In a preferred embodiment, wherein in step (2), the reaction is performed at 20° C. to 60° C., preferably 30° C. to 40° C., and more preferably 37° C. for 12-48 hours, preferably 18-30 hours, and more preferably 20 hours.

The present invention also provides a sequencing method of 5-formyl cytosine at single-base resolution, comprising:

(i) labeling a DNA or RNA sample as described above;

(ii) amplifying and sequencing a labeling reaction system after completion of reaction to obtain a post-labeling sequencing result;

(iii) comparing the post-labeling sequencing result with a reference sequence map of DNA or RNA, and determining a base at a certain position as 5-formyl cytosine if the base at the same position in the sequence is read as cytosine in the reference sequence map and read as thymine after labeling.

In a preferred embodiment, the DNA or RNA sample is a trace sample, or a sample obtained from a single cell derived from an embryonic stem cell, a gamete, an early embryo, a cancer cell, a nerve cell or a blood cell, etc.

In a preferred embodiment, the labeling reaction system after completion of the reaction in step (ii) is directly subjected to amplification without purification.

In a preferred embodiment, a method for amplification is a MALBAC or scRRBS amplification method.

The present invention also provides an amplification system for DNA or RNA, comprising the labeling reaction system after completion of the reaction in the aforementioned step (ii).

The present invention also provides a kit for 5-formyl cytosine sequencing at single-base resolution, comprising a buffer solution with a pH of 7.5-9, malononitrile and an amplification-related reagent.

The present invention also provides a method for detecting 5-formyl cytosine quantitatively, comprising:

(a) sequencing known pattern sequences in a number of N with different content of 5-formyl cytosine according to the aforementioned sequencing method and determining a proportion of C-T conversion, wherein N≥2; the proportion of C-T conversion is a proportion of the base at the same position in the sequence read as cytosine C before labeling and read as thymine T after labeling;

(b) plotting a standard curve with the content of 5-formyl cytosine as the horizontal/vertical coordinate and the proportion of C-T conversion as the vertical/horizontal coordinate;

(c) sequencing DNA or RNA with unknown content of 5-formyl cytosine according to the aforementioned sequencing method, and determining the proportion of C-T conversion;

(d) determining the content of 5-formyl cytosine in the DNA or RNA with unknown content of 5-formyl cytosine, based on the proportion of C-T conversion determined in step (c) and the standard curve in step (b).

The present invention enables the labeling of 5-formyl cytosine in a single cell at single-base resolution utilizing a specific chemical reaction of the compound of formula $R_1$—$CH_2$—CN with 5-formyl cytosine. Further, the labeling method provided by the present invention allows sequencing analysis for 5-formyl cytosine in a DNA or RNA sample, so as to determine sequence distribution information of 5-formyl cytosine. Since the sodium bisulfite treatment is not carried out during the labeling process, DNA or RNA will not be damaged. The treatment with malononitrile also does not cause degradation of DNA or RNA. Further, the inventors unexpectedly discovered that during the process of sequencing analysis of 5-formyl cytosine in DNA or RNA, the labeling reaction system after completion of the reaction can be directly amplified without purification, thereby reducing the loss of DNA. Therefore, the method for sequencing analysis of 5-formyl cytosine provided by the present invention can be implemented at single cell level and allows sequencing at a single-base resolution level. The method is more suitable for a variety of trace samples and precious biological samples, such as embryonic stem cells, gametes or early embryos, cancer cells and nerve cells, etc.

DESCRIPTION OF THE DRAWINGS

In order to illustrate the embodiments of the present invention and the prior art more clearly, below are brief descriptions for the drawings used in the embodiments and prior art. It is obvious to those skilled in the art that the drawings in the following description are only some examples of the invention, and other drawings may be obtained from these drawings without any inventive efforts.

DESCRIPTION OF THE EMBODIMENT

Figure 1:
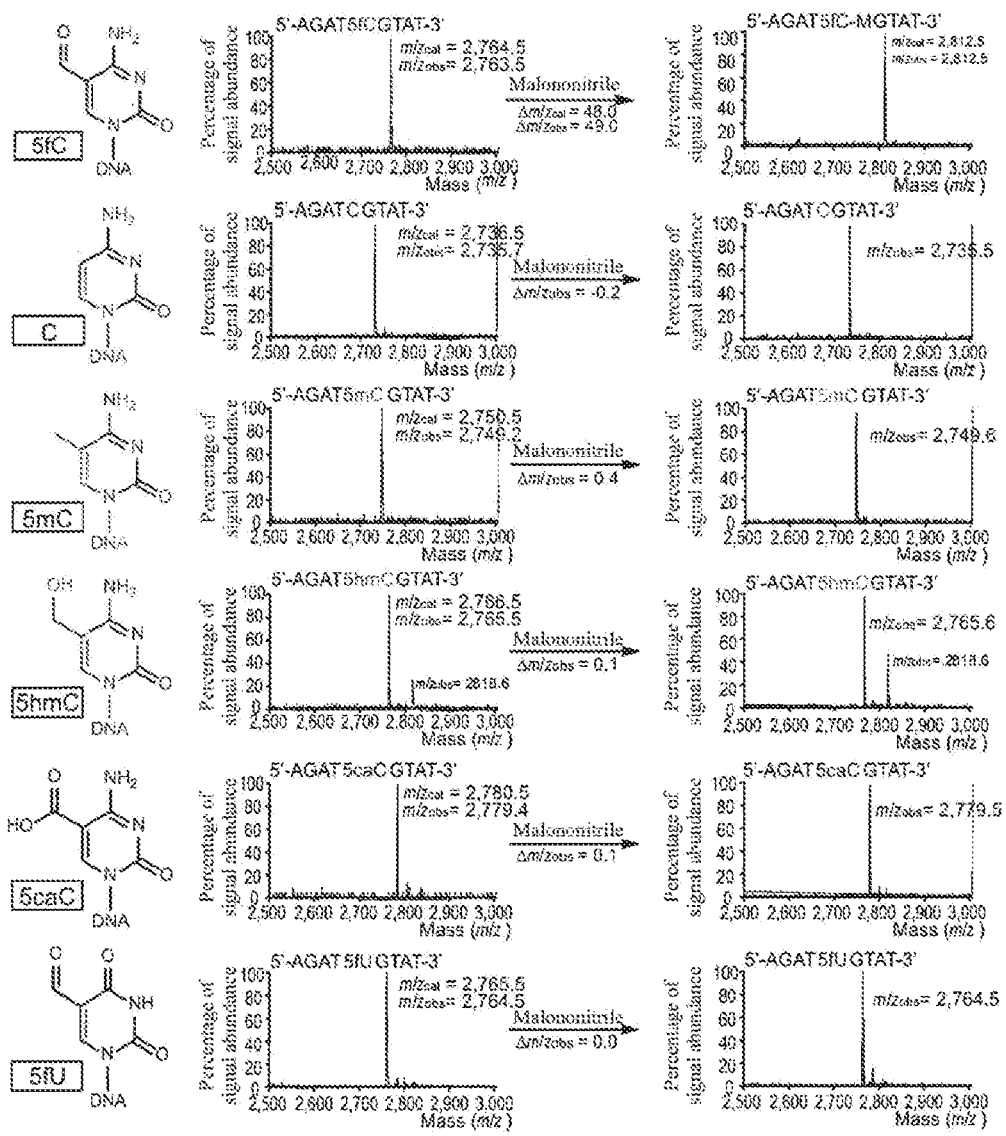
FIG. 1 is a mass spectrometry of 6 DNA sequences with 9 bases containing different cytosines in Example 1 before and after reaction with malononitrile, wherein 5fC labeled with malononitrile (M) is abbreviated as 5fC-M.

The present invention first provides a method for labeling 5-formyl cytosine, comprising:
(1) preparing a DNA or RNA sample;
(2) mixing the DNA or RNA sample with a buffer solution and a compound of formula $R_1$—$CH_2$—CN to obtain a labeling reaction system; and reacting the compound of formula $R_1$—$CH_2$—CN with 5-formyl cytosine in a DNA and RNA molecule to label 5-formyl cytosine; the reaction process is:

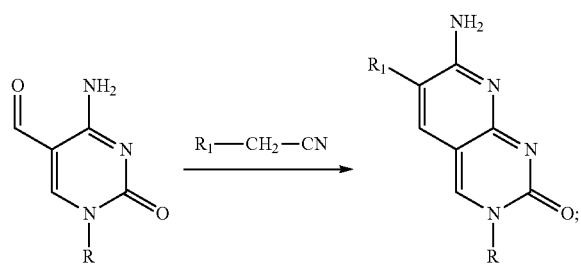

wherein, $R_1$ is an electron withdrawing group adjacent to $CH_2$, preferably —CN,

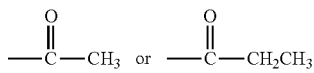

and the like, and more preferably —CN; R is a DNA or RNA molecule linked to 5-formyl cytosine; and the labeling reaction system has a pH of 7.5-9.

Conventional techniques in the art can be implemented for preparing the DNA or RNA sample in step (1). For example, one cell can be lysed by a conventional method to obtain the DNA or RNA sample. Step (1) is not particularly limited in the present invention.

The inventors unexpectedly discovered by research that when the labeling reaction system has a pH of 7.5-9, preferably 8-9, and more preferably 8, the yield of reaction in step (2) is as high as 98% or more. The yield herein refers to the ratio of the amount of the product of cyclization reaction between 5-formyl cytosine and the compound of formula $R_1$—$CH_2$—CN to the amount of 5-formyl cytosine before the reaction in the labeling reaction system, multiplied by 100%.

The inventors further discovered that, in the case where the compound of formula $R_1$—$CH_2$—CN is specifically malononitrile and malononitrile with the same concentration presents in the labeling reaction system, the yield in step (2) is significantly higher than that obtained with labeling reaction systems having a pH lower than 7. For example, when malononitrile has a concentration of 150 mM in the labeling reaction system with a pH of 7.5-9, preferably 8-9, more preferably 8, and the yield can be 99% or more. In some specific embodiments, the yield can be up to 99.1%. In some specific embodiments, the yield can be up to 99.2%. In some specific embodiments, the yield can be up to 99.3%. In some specific embodiments, the yield can be up to 99.4%. When the labeling reaction system is weakly acidic, the yield is slightly higher than 98% at most. Those skilled in the art understand that it is extremely difficult to increase the yield from 98% to 99%. Moreover, in the prior art, it has not been reported that the yield can be improved when the labeling reaction system is adjusted to be weakly basic. It can be seen that the present application achieves an unexpected technical effect. In one specific embodiment, a DNA sample or RNA sample is amplified and sequenced after it is reacted with the compound of formula $R_1$—$CH_2$—CN; and the yield can be calculated by the formula: $H_C/[H_C+H_T]\times 100\%$ according to the signal peak height of C (cytosine) ($H_C$) and the signal peak height of T (thymine) ($H_T$) of the corresponding site in the sequencing result peak map.

In one specific embodiment of the present invention, in order to obtain the labeling reaction system, a buffer solution, an aqueous solution containing the compound of formula $R_1$—$CH_2$—CN and a DNA or RNA sample are mixed together, so that the labeling reaction system has a pH of 7.5-9. The inventors discovered by experiments that the resulting labeling reaction system has a pH substantially consistent with that of the buffer solution added, when the compound of formula $R_1$—$CH_2$—CN or the DNA or RNA sample added into the labeling reaction system has a small volume relative to the buffer solution. In other words, it is obviously reasonable to regard the pH value of the buffer solution as the pH value of the labeling reaction system. For example, 2 ml of 50 mM $NH_4Ac$ solution and 10 mM Tris-HCl buffer solution as shown in Table 1 are separately prepared, the pH of which is adjusted with acetic acid or dilute hydrochloric acid to as shown in Table 1 (as shown in the column of "0 mM malononitrile"). 20 µl 15 M aqueous solution of malononitrile is added to each of the buffer solution so that malononitrile has a final concentration of 150 mM. The mixture is vortexed and homogenously mixed. The pH value of the buffer solution containing malononitrile is measured again by using a pH meter as shown in Table 1 (as shown in the column of "150 mM malononitrile"). As can be seen from Table 1, even if a small amount of other materials are added to the buffer solution, the pH of the buffer solution is hardly changed.

TABLE 1

| Buffer solution | 50 mM $NH_4Ac$ | 50 mM $NH_4Ac$ | 50 mM $NH_4Ac$ | 10 mM Tris-HCl | 10 mM Tris-HCl |
|---|---|---|---|---|---|
| 0 mM Malononitrile | 5.0 | 6.0 | 7.0 | 8.0 | 9.0 |
| 150 mM Malononitrile | 5.0 | 6.0 | 6.9 | 8.0 | 8.9 |

In the following examples of the present invention, other materials are added in an amount much smaller than that of the buffer solution. As verified by the inventors, the pH value of the buffer solution can be regarded as that of the labeling reaction system. In the following examples, the pH of the buffer solution is regarded as that of the labeling reaction system. In one specific embodiment, the buffer solution for preparing the labeling reaction system may be a Tris-HCl buffer solution (pH 7.5-9).

During the implementation of the technical solution of the present invention, the inventors unexpectedly found that, in the labeling reaction system, the concentration of the compound of formula $R_1$—$CH_2$—CN, such as malononitrile, also affects the yield. Without limited by any theory, it is concluded that: when the compound of formula $R_1$—$CH_2$—CN, for example malononitrile, has a concentration of 75-1500 mM, preferably 75-1000 mM, more preferably 75-500 mM, and most preferably 150 mM in the labeling reaction system, the labeling effect thereof, i.e. the yield, is better than that obtained when the concentration is below 75 mM or above 1500 mM. It should be noted that when the compound of formula $R_1$—$CH_2$—CN is used at a concentration of 75-1500 mM, it is excessive relative to 5-formyl cytosine in the labeling reaction system.

After the labeling reaction system is obtained, the labeling reaction system can be performed at a suitable temperature so that the compound of formula $R_1$—$CH_2$—CN is reacted with 5-formyl cytosine in a DNA or RNA molecule. In one specific embodiment, the labeling reaction system is reacted at 20° C. to 60° C. for 12 to 48 hours, preferably 18 to 30 hours, and more preferably 20 hours. In one specific embodiment, the labeling reaction system is reacted at 30° C. to 40° C. for 12 to 48 hours, preferably 18 to 30 hours, and more preferably 20 hours. In one specific embodiment, the labeling reaction system is reacted at 37° C. for 12 to 48 hours, preferably 18 to 30 hours, and more preferably 20 hours. During the reaction, the compound of formula $R_1$—$CH_2$—CN and the DNA or RNA sample can be homogenously mixed by a certain mixing method. For example, when the DNA or RNA sample is obtained by lysing a cell by a conventional method, the compound of formula $R_1$—$CH_2$—CN and the DNA or RNA sample can be homogenously mixed and incubated in a constant temperature mixer.

The present invention utilizes a specific chemical reaction of the compound of formula $R_1$—$CH_2$—CN with a 5-formyl cytosine to label 5-formyl cytosine. Moreover, since the compound of formula $R_1$—$CH_2$—CN does not react with C, 5mC, 5hmC, 5caC and 5fU (5-formyl uracil), the labeling method provided by the present invention can specifically label 5-formyl cytosine.

Based on the specific labeling of 5-formyl cytosine by using the compound of formula $R_1$—$CH_2$—CN, the present invention also provides a sequencing method of 5-formyl cytosine at single-base resolution, comprising:

(i) labeling a DNA or RNA sample as described above in the present invention;

(ii) amplifying and sequencing a labeling reaction system after completion of reaction to obtain a post-labeling sequencing result;

(iii) comparing the post-labeling sequencing result with a reference sequence map of DNA or RNA, and determining a base at a certain position as 5-formyl cytosine if the base at the same position in the sequence is read as cytosine in the reference sequence map and read as thymine after labeling. The "reference sequence map of DNA or RNA" is a disclosed sequence information of a DNA or RNA sample or genome obtained based on sequencing methods in the prior art. Those skilled in the art can obtain these DNA or RNA reference sequence maps, for example, from the Genomics Browser, University of California at Santa Cruz (UCSC Genome Browser) or GenBank.

In the reference sequence map, 5-formyl cytosine is still read as cytosine. The present invention takes advantage of the reaction product of 5-formyl cytosine and compound of formula $R_1$—$CH_2$—CN is mutated to thymine T during amplification process, thus the sequencing result is also shown as T. Sequence information of 5-formyl cytosine at single-base resolution can be identified by searching the C-T mutation site via comparison with the reference sequence map.

It should be noted that amplification and sequencing methods used in the present invention are the prior art in the field. For example, amplification can be performed by PCR methods commonly used, as well as MALBAC (Multiple Annealing and Looping Based Amplification Cycles), or scRRBS (single-cell reduced representative bisulfite sequencing), which is suitable for single cell. Sequencing can be carried out by using conventional techniques in the art. For example, the following may be used:

1) First-generation dideoxy base sequencing, which can utilize commercial sequencing platforms including a series of instruments of the first generation sequencing platform of ABI;

2) Second-generation high-throughput sequencing technology, which can utilize commercial sequencing platforms including: series of sequencing platforms of Illumina, including but not limited to Miseq, Hiseq 2000, Hiseq 2500, NextSeq 500, Hiseq X, etc.; sequencing platforms of pyro-sequencing of Roche, for example, but not limited to, GS FLX; SOLiD sequencing platform of ABI, for example, but not limited to, SOLiD 5500;

3) Third-generation single-molecule sequencing technology, which can utilize commercial sequencing platforms including: SMRT sequencing platform of Pacific Biosciences, for example but not limited to SMRT RSII; nanopore single-molecule sequencing platform of Oxford Nanopore Technologies, such as MinION platform; HeliScope platform of Helicos Biosciences.

It should be noted that the method of obtaining a DNA or RNA sample from a cell is a conventional technique in the art, and it is not described in detail in the present invention. In one specific embodiment, the DNA or RNA sample is a trace sample, or a sample obtained from a single cell, which can be derived from, but not limited to an embryonic stem cell, a gamete, an early embryo, a cancer cell, a nerve cell or a blood cell, etc.

Based on the sequencing method of 5-formyl cytosine at single-base resolution provided by the present invention, the present invention also provides a kit for sequencing 5-formyl cytosine at single-base resolution. The kit comprises a buffer solution with a pH value of 7.5-9, preferably 8-9, and more preferably 8, malononitrile and an amplification related reagent. It can be understood that the amplification related reagent is the sum of various materials required for amplification. For example, the amplification related reagent may include materials related to DNA or RNA amplification, such as a polymerase, a primer, a dNTP, a buffer liquid, and water, etc., but may not include an amplified subject, such as a DNA or RNA molecule. Specific materials can be selected by those skilled in the art as desired, which will not be described in detail in the present invention.

The inventors unexpectedly discovered during the experiment that after labeling 5-formyl cytosine according to the method provided by the present invention, the maring reaction system can be directly amplified. The remaining compound of formula $R_1$—$CH_2$—CN and the other materials in the labeling reaction system will not affect the amplification, and may even facilitate the amplification. Therefore, in one specific embodiment, the labeling reaction system in the above step (ii) can be directly amplified without purification. Since the purification step is omitted, DNA or RNA loss caused in the purification step can be effectively avoided. The method of the invention is therefore suitable for the detection of a sample with a small amount of DNA or RNA, such as a DNA or RNA sample derived from a single cell.

On this basis, the present invention also provides an amplification system for DNA or RNA, comprising the labeling reaction system after the completion of the reaction in the step (ii) in the above sequencing method of 5-formyl cytosine at single-base resolution.

Based on the sequencing method at single-base resolution provided by the present invention, the present invention also provides a method for quantitatively detecting 5-formyl cytosine, comprising:

(a) sequencing a known pattern sequence in a number of N with different content of 5-formyl cytosine according to the aforementioned sequencing method and determining a proportion of C-T conversion, wherein N≥2, preferably N≥3, and more preferably N≥5;

the proportion of C-T conversion is that of the base at the same position in the sequence read as cytosine C before labeling and read as thymine T after labeling;

(b) plotting a standard curve with the content of 5-formyl cytosine as the horizontal/vertical coordinate and the proportion of C-T conversion as the vertical/horizontal coordinate;

(c) sequencing DNA or RNA with unknown content of 5-formyl cytosine according to the aforementioned sequencing method, and determining the proportion of C-T conversion;

(d) determining the content of 5-formyl cytosine in the DNA or RNA with unknown content of 5-formyl cytosine, based on the proportion of C-T conversion determined in step (c) and the standard curve in step (b).

Herein, the pattern sequence is a natural or synthetic DNA or RNA sequence, wherein the base and the modified base thereof on each position are known or pre-designed.

In one specific embodiment, the content of 5-formyl cytosine may be a proportion of 5-formyl cytosine with respect to all cytosines, which may be expressed specifically in percentage, and may be expressed by 5fC/C.

The technical solutions in the examples of the present invention will be clearly and completely described in the following with reference to the accompanying drawings in the examples of the present invention. It is obvious that the described examples are only a part of the examples of the present invention, but not all of examples. All other examples obtained by those skilled in the art based on the examples of the present invention without creative efforts are within the scope of the present invention.

The pattern DNA sequences involved in the following examples are shown in Table 2.

TABLE 2

| Oligo ID NO. | Sequence (5'→3') | Referred to as | SEQ ID NO. |
|---|---|---|---|
| 1 | AGAT5fCGTAT | 5fC-9mer | |
| 2 | AGATCGTAT | C-9mer | |
| 3 | AGAT5mCGTAT | 5mC-9mer | |
| 4 | AGAT5hmCGTAT | 5hmC-9mer | |
| 5 | AGAT5caCGTAT | 5caC-9mer | |
| 6 | AGAT5fUGTAT | 5fU-9mer | |
| 7 | CCTCACCATCTCAACCAATATTATATTACGCGTATAT5fCGCGTATTTCGCGTTATAATATTGAGGGAGAAGTGGTGA | 5fC-76mer | 1 |

Example 1

Determining the specificity of the compound of formula $R_1$—$CH_2$—CN for labeling 5-formyl cytosine with, e.g., malononitrile Pattern DNA sequences of 9 bases (Oligo ID No. 1-6) with single position modified to 5fC, 5mC, 5hmC, 5caC, C and 5-formyl uracil (5fU) were chemically synthesized, by using phosphoramidite monomer purchased from GlenResearch and Expetide DNA/RNA solid phase synthesizer. These pattern DNA sequences were deprotected and purified as illustrated, and the obtained pattern sequences were further purified via ethanol precipitation. 4 μg of purified pattern sequence was added to a 1.5 ml Eppendorf tube, then added with 10 μL of 100 mM Tris-HCl (pH 8.0) and 10 μL of 1.5 M aqueous solution of malononitrile, further added with water so that the volume of the labeling reaction system was 100 μL, and the content of malononitrile was 150 mM. The reaction system was homogenously mixed and incubated in an Eppendorf Thermomixer at 37° C., 850 rpm for 20 hours. After completion of the reaction, the labeled pattern DNA sequences were purified via ethanol precipitation and further desalted by using a Bio-rad spin-6 column. The purified DNA was subjected to mass spectrometry by using MALDI-TOF (ABI, 7500).

The mass spectrometry results are shown in FIG. 1. After the reaction of the compound of malononitrile with the 5fC-containing pattern DNA sequence, the relative molecular mass of the pattern DNA increased by 49.0, which was consistent with the calculated value, indicating that malononitrile can react with 5fC on the pattern DNA sequence. At the same time, the relative molecular mass of the pattern DNA did not change after the reaction of the compound of malononitrile with the pattern sequences containing C, 5mC, 5hmC, 5caC and 5fU, indicating that malononitrile can not react with C, 5mC, 5hmC, 5caC and 5fU. The above results indicate that the compound malononitrile can specifically label 5fC. The same conclusion can be obtained for other compounds R$_1$—CH$_2$—CN, which will not be described in detail in the present invention.

Examples 2-12

Labeling pattern sequence containing 5-formyl cytosine with malononitrile and sequencing

Example 2

Figure 2:
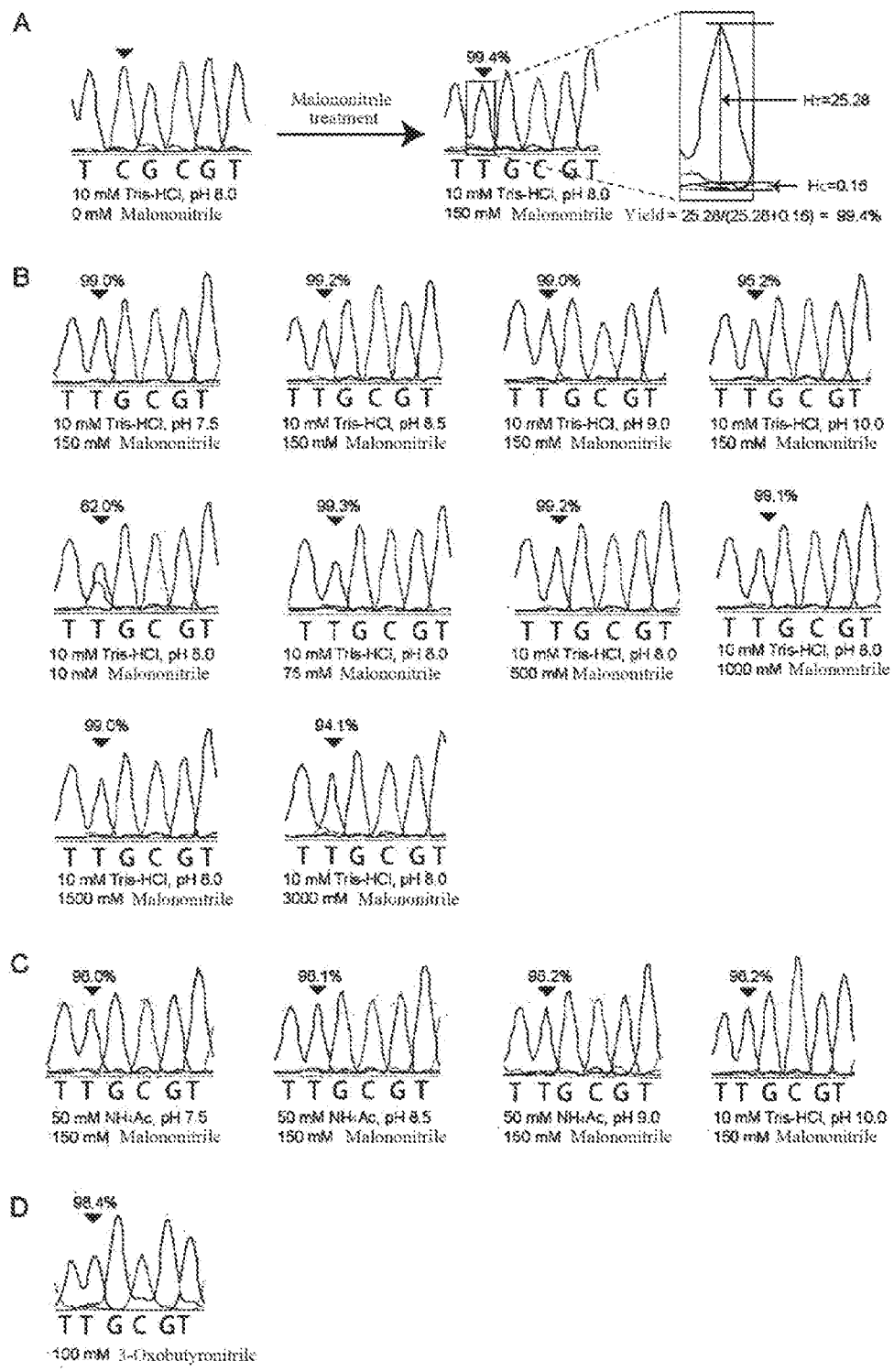
FIG. 2A shows the results of labeling 5-formyl cytosine with malononitrile in Example 2.
FIG. 2B shows the results of labeling 5-formyl cytosine with malononitrile in Examples 3-12.
FIG. 2C shows the results of labeling 5-formyl cytosine with malononitrile in Comparative Examples 1-4.
FIG. 2D shows the results of labeling 5-formyl cytosine with 3-oxobutyronitrile in Example 13.

Pattern DNA sequence of 76 bases (Oligo ID No. 7) with a single position modified to 5fC was chemically synthesized by using phosphoramidite monomer purchased from GlenResearch and Expetide DNA/RNA solid phase synthesizer. This pattern DNA sequence was deprotected and purified as illustrated, and the obtained pattern sequence was further purified via ethanol precipitation. 1 μg of purified pattern sequence was added to a 1.5 ml Eppendorf tube, then added with 2 μL of 100 mM Tris-HCl (pH 8.0) and 2 μL of 1.5 M aqueous solution of malononitrile, further added with water so that the volume of the labeling reaction system was 20 μL, and the content of malononitrile was 150 mM. The reaction system was homogenously mixed and incubated at 37° C., 850 rpm for 20 hours in an Eppendorf Thermomixer (constant temperature mixer) in the dark. After labeling, 25 μL of 2× MightyAmp Buffer (Takara) was directly added to 20 μL of the reaction liquid and homogenously mixed. 2 μL of forward and reverse primers (primer sequences are shown in Table 3) and 1 μL of MightyAmp DNA Polymerase (Takara) were added so that the final volume of the system was 50 μL. PCR amplification was performed. The amplified product with a single band was detected by Sanger sequencing by using sequencing primers (primer sequences are shown in Table 3). The yield was calculated with C (cytosine) signal peak heights (H$_C$) and T (thymine) signal peak heights (H$_T$) at corresponding positions in the peak map of the sequencing results, measured by SnapGene software, according to formula H$_C$/[H$_C$+H$_T$]×100%. As shown in FIG. 2A, it can be seen that H$_C$=0.16, H$_T$=25.28, and yield=H$_C$/[H$_C$+H$_T$]×100%=99.4%.

TABLE 3

| | (5'→3') | SEQ ID NO. |
|---|---|---|
| Forward primer | CCTCACCATCTCAACCAATATTATATT | 2 |
| Reverse primer | CTCCGACATTATCACTACCATCAACCACCCATCCTACCTGG ACTACATTCTTATTCAGTATTCACCACTTCTCCCTCAAT | 3 |
| Sequencing primer | CTCCGACATTATCACTACCA | 4 |

Examples 3-12

5-formyl cytosine was labeled with malononitrile according to the method in Example 2, with various pH value of the Tris-HCl buffer solution and various concentration of malononitrile in the labeling reaction system. The various values and yields obtained are shown in Table 4 and FIG. 2B.

Comparative Examples 1-4

5-formyl cytosine was labeled with malononitrile according to the method in Example 2, except that the pH of the buffer solution was adjusted to weakly acidic. The specific values adjusted and yields obtained are shown in Table 4 and FIG. 2C.

TABLE 4

| | pH Value | Concentration of malononitrile | Yield |
|---|---|---|---|
| Example3 | 7.5 | 150 mM | 99.0% |
| Example4 | 8.5 | 150 mM | 99.2% |
| Example5 | 9.0 | 150 mM | 99.0% |
| Example6 | 10.0 | 150 mM | 95.2% |
| Example7 | 8.0 | 10 mM | 62.0% |
| Example8 | 8.0 | 75 mM | 99.3% |
| Example9 | 8.0 | 500 mM | 99.2% |
| Example10 | 8.0 | 1000 mM | 99.1% |
| Exantple11 | 8.0 | 1500 mM | 99.0% |
| Example12 | 8.0 | 3000 mM | 94.1% |
| Comparative Example1 | 5.0 | 150 mM | 98.0% |
| Comparative Example2 | 6.0 | 150 mM | 98.1% |
| Comparative Example3 | 7.0 | 150 mM | 98.2% |
| Comparative Example4 | 7.0 | 150 mM | 98.2% |

Note:
The buffer solution in Comparative Example 3 was NH$_4$Ac buffer solution.
The buffer solution in Comparative Example 4 was Tris-HCl buffer solution.

Example 13

Labeling pattern sequence containing 5-formyl cytosine with 3-oxobutyronitrile and sequencing Pattern DNA sequences of 76 bases (Oligo ID No. 7) with a single position modified to 5fC was chemically synthesized by using phosphoramidite monomer purchased from GlenResearch and Expetide DNA/RNA solid phase synthesizer. This pattern DNA sequences was deprotected and purified as illustrated, and the obtained pattern sequence was further purified via ethanol precipitation. 1 μg of the purified pattern sequence was added to a 1.5 ml Eppendorf tube, then added with 2 μL of 100 mM Tris-HCl (pH 7.5) and 2 μL of 1.0 M aqueous solution of 3-oxobutyronitrile

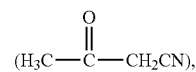

further added with water so that the volume of the labeling reaction system was 20 μL, and the content of 3-oxobutyronitrile was 100 mM. The reaction system was homogenously mixed and incubated at 60° C., 850 rpm for 48 hours in an Eppendorf Thermomixer (constant temperature mixer) in the dark. After labeling, 25 μL of 2× MightyAmp Buffer (Takara) was directly added to 20 μL of the reaction liquid and homogenously mixed. 2 μL of forward and reverse primers (primer sequences are shown in Table 3) and 1 μL of MightyAmp DNA Polymerase (Takara) were added so that the final volume of the system was 50 μL. PCR amplification was performed. The amplified product with a single band was detected by Sanger sequencing by using sequencing primers (primer sequences are shown in Table 3). The yield was calculated with C (cytosine) signal peak heights ($H_C$) and T (thymine) signal peak heights ($H_T$) at corresponding positions in the peak map of the sequencing results, measured by SnapGene software, according to formula $H_C/[H_C+H_T]\times100\%$. As shown in FIG. 2D, it can be seen that $H_C=0.41$, $H_T=25.12$, and yield=$H_C/[H_C+H_T]$ =98.4%.

Example 14

5-formyl cytosine was labeled with malononitrile according to the method in Example 2, expect that the reaction temperature was adjusted to 20° C. and the reaction time was adjusted to 48 hours. The yield was 98.7%.

Example 15

5-formyl cytosine was labeled with malononitrile according to the method in Example 2, except that the reaction temperature was adjusted to 60° C. and the reaction time was adjusted to 12 hours. The yield was 99.0%.

Example 16

Verification of the advantages of the reaction system without purification after labeling with compound of formula $R_1$—$CH_2$—CN, e.g. malononitrile, for DNA amplification Pattern DNA sequences of 76 mer (Oligo ID No. 7) with a single position modified to 5fC was chemically synthesized by using phosphoramidite monomer purchased from GlenResearch and Expetide DNA/RNA solid phase synthesizer. This pattern DNA sequence was deprotected and purified as illustrated, and the obtained pattern sequence was further purified via ethanol precipitation. 20 ng of purified pattern sequence was added to a 1.5 ml Eppendorf tube, then added with 4 μL of 100 mM Tris-HCl (pH 8.0) and 4 μL of 1.5 M aqueous solution of malononitrile, further added with water so that the volume of the labeling reaction system was 40 μL, and the content of malononitrile was 150 mM. The reaction system was homogenously mixed and incubated at 37° C., 850 rpm for 20 hours in an Eppendorf Thermomixer in the dark. After labeling, half of the reaction solution (20 μL) was taken and purified using a Vistech DNA Purification Recycling Kit, which was used as a purified sample group. The remaining half of the reaction solution was used as an unpurified group. 25 μL of 2×MightyAmp Buffer (Takara) was added to the purified group and unpurified group and homogenously mixed. 2 oL of forward and reverse primers (primer sequences are shown in Table 3) and 1 μL of MightyAmp DNA Polymerase (Takara) were added so that the final volume of the system was 50 μL. Amplification was performed. The amplification was suspended at the end of each amplification cycles of 1, 3, 5, 7, 9, 11 and 13, and 2.5 μL of the amplified sample was taken after homogenously mixing. Amplifications were continued until 15 amplification cycles were completed. The content of amplification products obtained with different cycle numbers were analyzed by gel electrophoresis. The results are shown in FIG. 3.

Figure 3:
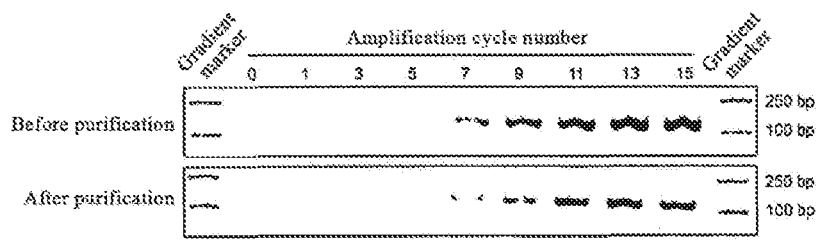
FIG. 3 shows the comparative result of amplified products of the reaction system after labeling with malononitrile with or without purification in Example 16.

As can be seen from FIG. 3, as the amplification cycle number increases, the relative content of amplification products increase both in the purified group and unpurified group. The amplification product bands can be clearly observed for the unpurified group after completion of 5 cycles of amplification, while no visible amplification product band was observed for the purified group after completion of 5 cycles of amplification. After completion of 15 cycles of amplification, the content of amplification product in the unpurified group was significantly higher than that in the purified group. The above results indicate that the labeling system obtained with malononitrile can be amplified without purification. Fewer cycle numbers may be needed to amplify desired product, or more desired product can be amplified by using the same amplification cycle number, compared with the control purified group. Therefore, a labeling reaction system obtained with malononitrile without purification is more advantageous for DNA amplification. The same conclusion can be obtained for other compounds $R_1$—$CH_2$—CN, which will not be described in detail in the present invention.

Example 17

Figure 4:
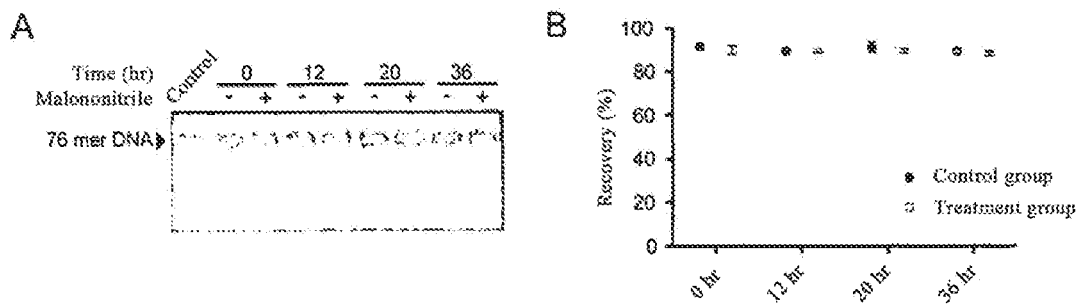
FIGS. 4A and 4B show the verification results that the malononitrile labeling reaction does not degrade DNA in Example 17.

Verification of no DNA degradation will be observed in the labeling reaction with compound of formula $R_1$—$CH_2$—CN e.g. malononitrile 1 μg of the pattern sequence (Oligo ID NO. 7) purified via ethanol precipitation was added to a 1.5 ml Eppendorf tube, then added with 5 μL of 100 mM Tris-HCl (pH 8.0) and 5 μL of 1.5 M aqueous solution of malononitrile were added, further added with water so that the volume of the labeling reaction system was 50 μL, and the content of malononitrile was 150 mM, which is used as a malononitrile-treated group. 1 μg of the pattern sequence (Oligo ID NO. 7) purified via ethanol precipitation and 10 mM Tris-HCl (pH 8.0) were added to a 1.5 ml Eppendorf tube so that the final volume is 50 μL, which is used as an untreated group. The reaction system was homogenously mixed and incubated in an Eppendorf Thermomixer at 37° C., 850 rpm for 0, 12, 20 and 36 hours in the dark. 5 μL reacted sample was taken and measured by gel electrophoresis for relative content, and the results are shown in FIG. 4A. DNA being not incubated was used as a control group. As can be seen from FIG. 4A, the treated group and untreated group exhibited the same band size and concentration as the control group after 0, 12, 20, and 36 hours, without observation of short fragments (FIG. 4A).

1 μg of mouse embryonic stem cell genomic DNA, 10 mM Tris-HCl (pH 8.0) and 150 mM malononitrile were added to a 1.5 ml Eppendorf tube so that the final volume of the reaction system was 50 μL, which is used as a malononitrile-treated group. 1 μg of mouse embryonic stem cell genomic DNA and 10 mM Tris-HCl (pH 8.0) were added to a 1.5 ml Eppendorf tube so that the final volume was 50 μL, which is used as a control group. The reaction system was homogenously mixed and incubated in an Eppendorf Thermomixer at 37° C., 850 rpm for 0, 12, 20 and 36 hours in the dark. After the completion of the incubation, 1 μg of glycogen (Invitrogen), 5 μL of sodium acetate (pH 5.4), and 168 μL of absolute ethanol pre-cooled on ice were added for purification via ethanol precipitation. After purification, genomic DNA recovery rate was measured and calculated by using Nanodrop, and the results are shown in FIG. 4B.

As can be seen from FIG. 4B, the treated group and control group have substantially identical genomic DNA recovery rates after 0, 12, 20 and 36 hours of incubation, indicating that malonitrile treatment does not cause loss of genomic DNA. The same conclusion can be obtained for other compounds R₁—CH₂—CN, which will not be described in detail in the present invention herein.

Example 18

Figure 5:
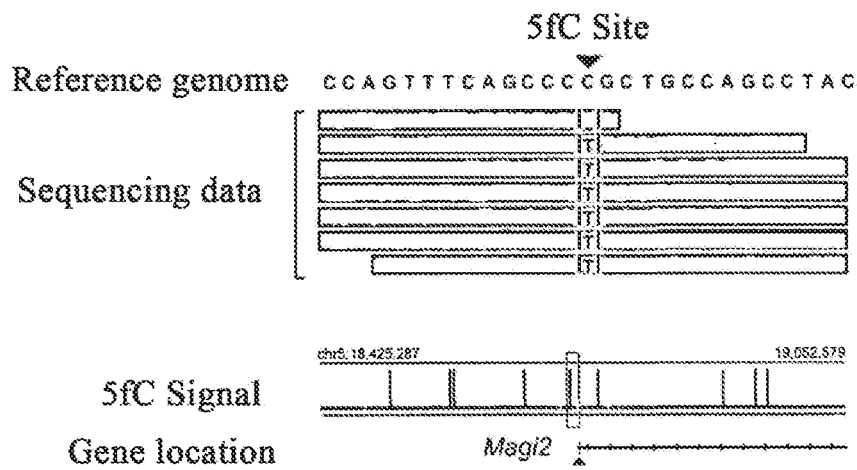
FIG. 5 shows the comparative result of partial sequencing of Examples 18 and 19.

Detection of whole genome 5fC at single cell and single-base resolution by labeling 5-formyl cytosine with malononitrile combined with MALBAC single-cell amplification technology One mouse embryonic stem cell was picked up and transferred to 4 µL of lysate (20 mM Tris, pH 8.0, 2 mM EDTA, 20 mM KCl, 0.3% Triton-X100) under a microscope. 20 units of protease were added to the lysate. The cells were lysed by incubating at 50° C. for 3 hours. 0.5 µL of 1.5 M compound of malononitrile was added to 5 µL of single cell lysate, to which 15 µL of mineral oil was added for liquid sealing. The reaction system was incubated at 37° C., 850 rpm with shaking (Eppendorf, Thermomixer) for 20 hours in the dark to label 5-formyl cytosine in the single cell genome. The labeled DNA can be amplified by using the MALBAC single cell genomic amplification technique (primer sequences are shown in Table 5): for labeled single cell lysates, 11 cycles of pre-amplification and 15 cycles of exponential amplification were required to obtain 500 ng to 1 µg of amplification products. During amplification, the labeled 5-formyl cytosine was read as thymine T and can therefore be used for 5-formyl cytosine detection at single-base resolution. A library was constructed for amplification product by using the NEBNext Ultra DNA Library Prep Kit, and the amplification product was sequenced using the Illumina HiSeq platform. The sequencing results were compared with the reference genome (obtained from the UCSC Genome Browser or GenBank). A part of the comparison results are shown in FIG. 5. As can be seen from FIG. 5, the position without 5fC completely matches with the reference genome; the position with 5fC is converted compared to the reference genome, i.e., shown as C in the reference genome and as T in the sequenced data.

This result indicates that the latter is 5fC. In addition, since the location of genes is also indicated in the reference genome, the specific location of 5fC on the genome is also obtained. In FIG. 5, each black vertical line in the 5fC signal map represents one detected 5fC position; there is a 5fC position in the promoter region on the left side (inside the box on the left of Magi2 gene in the figure) of the Magi2 gene (its starting position indicated by an inverted triangle).

TABLE 5

| | (5'→3') | SEQ ID NO. |
|---|---|---|
| MALBAC Primer | GTGAGTGATGGTTGAGGTAGTGTGGAG NNNNNNNN | 5 |

Example 19

Detection of simplified expressed 5fC at single cell and single-base resolution by labeling 5-formyl cytosine with malononitrile combined with scRRBS technology One mouse embryonic stem cell was picked up and transferred to 4 µL of lysate (20 mM Tris, pH 8.0, 2 mM EDTA, 20 mM KCl, 0.3% Triton-X100) under a microscope. 20 units of protease were added to the lysate. The cell was lysed by incubating at 50° C. for 3 hours. 9 U DpnII (NEB) was added to the single cell lysate and incubated for 3 hours at 37° C. 5 U Klenow Polymerase (3'-5' exo-, Fermentas) was added, incubated at 37° C. for 30 minutes, and incubated at 65° C. for 20 minutes for inactivation. The linker sequence and the complementary chain thereof (sequences are shown in Table 6) and 30 U of high concentration of T4 DNA ligase (Fermentas) were added, ligated overnight (at least 8 hours) at 10° C. and incubated at 60° C. for 30 minutes for inactivation. At this time, the single cell lysate system was 9 µL, added with 1 µL of 1.5 M compound of malononitrile, followed by 15 µL of mineral oil for liquid sealing. The reaction system was incubated at 37° C., 850 rpm with shaking (Eppendorf, Thermomixer) for 20 hours in the dark to label 5-formyl cytosine in the single cell genome. The labeled single cell lysate was amplified by using MightyAmp DNA polymerase (Takara) (amplification primers are as shown in Table 6): about 500 ng to 1 µg of amplification product was obtained after 35 cycles of exponential amplification. The appropriate fragments (~200-700 bp) were isolated and purified by gel electrophoresis, and sequenced with Illumina HiSeq 4000 after excess linker was removed.

The sequencing results were compared with the reference genome (obtained from the UCSC Genome Browser or GenBank), the result of which is the same as that in Example 18 (as shown in FIG. 5).

TABLE 6

| | (5'→3') | SEQ ID NO. |
|---|---|---|
| Linker sequence | AATGATACGGCGACCACCGAGATCTACACTCTT TCCCTACACGACGCTCTTCCGATCT | 6 |
| Complimentary chain of linker sequence | GATCGGAAGAGCACACGTCTGAACTCCAGTCA CATCACGATCTCGTATGCCGTCTTCTGCTTG | 7 |
| Forward primer | AATGATACGGCGACCACCGA | 8 |
| Reverse primer | CAAGCAGAAGACGGCATACGA | 9 |

Example 20

Figure 6:
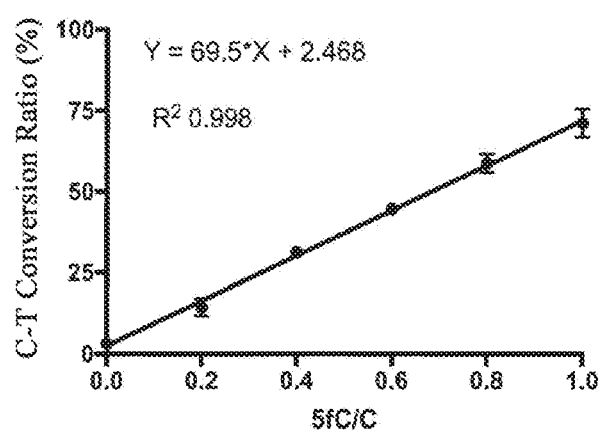
FIG. 6 shows a standard curve drawn in Example 20.

100 ng pattern sequence (the pattern sequence consisted of the same sequences with or without 5fC, and 6 groups of parallel reaction systems contained 0%, 20%, 40%, 60%, 80% and 100% of the sequence containing 5-formyl cytosine, respectively, the sequences are as shown in Table 7), 5 μL of 1.5 M aqueous solution of compound of malononitrile, 5 μL of 100 mM Tris-HCl (pH 8.0) were added to a 50 μL reaction system, and added with water to obtain a volume of 50 μL. The reaction system was incubated at 37° C., 850 rpm with shaking (Eppendorf, Thermomixer) for 20 hours in the dark to label 5-formyl cytosine. The labeled single cell lysate was amplified by using MightyAmp DNA polymerase (Takara). A library was constructed for amplification product using the NEBNext Ultra DNA Library Prep Kit, and the amplification product was sequenced by using the Illumina HiSeq 4000 platform. A standard curve was determined by statistically analyze the proportion of C-T conversion, which is observed in pattern sequences with different modification proportion, as shown in FIG. 6.

100 ng of test sequence with 5fC content of 50% (obtained by mixing pattern sequences with and without 5fC in a ratio of 1:1, the sequences are as shown in Table 7), 5 μL of 1.5 M compound of malononitrile and 5 μL of 100 mM Tris-HCl (pH 8.0) were added to a 50 μL reaction system, added with water to obtain a volume of 50 μL. The reaction system was incubated at 37° C., 850 rpm with shaking (Eppendorf, Thermomixer) for 20 hours in the dark to label 5-formyl cytosine. The labeled single cell lysate was amplified by using MightyAmp DNA polymerase (Takara). A library was constructed for amplification product by using the NEBNext Ultra DNA Library Prep Kit, and the amplification product is sequenced by using the Illumina HiSeq 4000 platform. The sequencing results were compared with the pattern sequence. The statistical results shows that the ratio of 5fC positions with a reading of T ($n_T$) to all bases with readings of both C and T ($n_C+n_T$) were: $n_T/(n_C+n_T)$ *100%=38%, substituted into the standard curve of FIG. 6, the fitted equation is: y=69.5*x+2.468, where x is the content of 5fC and y is the measured value of $n_T/(n_C+n_T)$. The 5fC content is calculated as: 5fC %=[$n_T/(n_C+n_T)$−2.468]/69.5*100%=(38−2.468)/69.5*100%=51.1%.

TABLE 7

| | (5'→3') | SEQ ID NO. |
|---|---|---|
| Pattern sequence with 5fC | CCTCACCATCTCAACCAATATTATATTACGCGTATAT5fCGCGTATTTCGCGTTATAATATTGAGGGAGAAGTGGTGAATACTGAATAAGAATGTAGTCCAGGTAGGATGGGTGGTTGATGGTAGTGATAATGTCGGAG | 10 |
| Pattern sequence without 5fC | CCTCACCATCTCAACCAATATTATATTACGCGTATATCGCGTATTTCGCGTTATAATATTGAGGGAGAAGTGGTGAATACTGAATAAGAATGTAGTCCAGGTAGGATGGGTGGTTGATGGTAGTGATAATGTCGGAG | 11 |

The above are only preferred examples of the present invention, and are not intended to limit the present invention. Any modifications, equivalents, improvements, etc., which are made within the spirit and principles of the present invention, should be included within the scope of the present invention.

---

The invention claimed is:

1. A method for labeling 5-formyl cytosine, comprising:
   (1) preparing a DNA or RNA sample;
   (2) mixing the DNA or RNA sample with a buffer solution and a compound of formula $R_1$—$CH_2$—CN to obtain a labeling reaction system; and reacting the compound of formula $R_1$—$CH_2$—CN with 5-formyl cytosine in a DNA or RNA molecule to label 5-formyl cytosine according to the following reaction scheme:

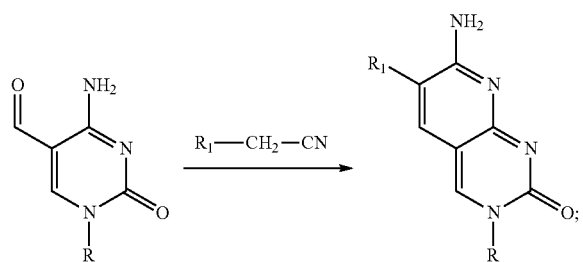

wherein, $R_1$ is an electron withdrawing group adjacent to $CH_2$; R is a DNA or RNA molecule linked to 5-formyl cytosine; and the labeling reaction system has a pH of 7.5-9, wherein the concentration of the compound of formula $R_1$—$CH_2$—CN in the labeling reaction system is in the range from 75 mM to 1500 mM.

2. The method according to claim 1, wherein the labeling reaction system has a pH of 8-9.

3. The method according to claim 1, wherein in step (2), the reaction is performed at 20° C. to 60° C. for 12-48 hours.

4. A sequencing method of 5-formyl cytosine at single-base resolution, comprising:
   (i) labeling a DNA or RNA sample by using the method according to claim 1;
   (ii) amplifying and sequencing a labeling reaction system after completion of reaction to obtain a sequencing result of a labeled sample; and
   (iii) comparing the sequencing result of the labeled sample with a reference sequence map of DNA or RNA, and determining a base at a certain position in the sample as 5-formyl cytosine if the base at the same position in the reference sequence map is read as cytosine and the base at the same position in the labeled sample is read as thymine.

5. The method according to claim 4, wherein the DNA or RNA sample is a trace sample or a sample obtained from a single cell.

6. The method according to claim 4, wherein the labeling reaction system after completion of the reaction in the step (ii) is directly subjected to amplification without purification.

7. The method according to claim 4, wherein a method for amplification is a MALBAC or scRRBS amplification method.

8. An amplification system for DNA or RNA, comprising the labeling reaction system after completion of the reaction in step (ii) according to claim 4.

9. A kit for sequencing 5-formyl cytosine at single-base resolution, comprising a buffer solution with a pH of 7.5-9, malononitrile and an amplification-related reagent, wherein the concentration of malononitrile in the labeling reaction system is in the range from 75 mM to 1500 mM.

10. A method for detecting 5-formyl cytosine quantitatively, comprising:
    (a) sequencing N known pattern sequences with different content of 5-formyl cytosine by using the method according to claim 5 and determining a proportion of C-T conversion, wherein N≥2; the proportion of C-T conversion is a proportion of the number of bases read as cytosine C before labeling and read as thymine T after labeling at the same position in the sequence relative to the total number of the bases read as cytosine and thymine after labeling;
    (b) plotting a standard curve with the content of 5-formyl cytosine as the horizontal/vertical coordinate and the proportion of C-T conversion as the vertical/horizontal coordinate;
    (c) sequencing DNA or RNA with an unknown content of 5-formyl cytosine by using the method according to claim 5, and determining the proportion of C-T conversion; and
    (d) determining the content of 5-formyl cytosine in the DNA or RNA with the unknown content of 5-formyl cytosine, based on the proportion of C-T conversion determined in step (c) and the standard curve in step (b).

11. The method according to claim 1, wherein, $R_1$ is —CN,

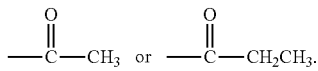

12. The method according to claim 1, wherein the labeling reaction system has a pH of 8.

13. The method according to claim 1, wherein the concentration of the compound of formula $R_1$—$CH_2$—CN in the labeling reaction system is in the range from 75 mM to 1000 mM.

14. The method according to claim 1, wherein the concentration of the compound of formula $R_1$—$CH_2$—CN in the labeling reaction system is in the range from 75 mM to 500 mM.

15. The method according to claim 1, wherein in step (2), the reaction is performed at 30° C. to 40° C.

16. The method according to claim 1, wherein in step (2), the reaction is performed at 37° C.

17. The method according to claim 1, wherein in step (2), the reaction is performed for 18-30 hours.

18. The method according to claim 1, wherein in step (2), the reaction is performed for 20 hours.

19. The method according to claim 4, wherein the single cell is derived from an embryonic stem cell, a gamete, an early embryo, a cancer cell, a nerve cell or a blood cell.

* * * * *